United States Patent [19]
Kyi

[11] 3,960,869
[45] June 1, 1976

[54] PREPARATION OF 2-CHLOROPYRIDINE BY HYDROGENOLYSIS

[75] Inventor: Roland R. Kyi, North Haven, Conn.

[73] Assignee: Olin Corporation, New Haven, Conn.

[22] Filed: Mar. 4, 1974

[21] Appl. No.: 447,611

[52] U.S. Cl. .......................... 260/290 HL; 252/472
[51] Int. Cl.² ...................................... C07D 213/89
[58] Field of Search .................................. 260/290

[56] References Cited
UNITED STATES PATENTS 3,355,456  11/1967  Sexton ............................... 260/290

*Primary Examiner*—Harry I. Moatz
*Attorney, Agent, or Firm*—Robert L. Andersen; Eugene Zagarella, Jr.

[57] ABSTRACT

A process is provided for the preparation of 2-chloropyridine by the liquid phase hydrogenolysis of 2,6-dichloropyridine in the presence of a selected transition metal catalyst and a strong base.

8 Claims, No Drawings

PREPARATION OF 2-CHLOROPYRIDINE BY HYDROGENOLYSIS

This invention relates to the preparation of 2-chloropyridine by hydrogenolysis. More particularly, this invention involves the selective liquid phase hydrogenolysis of 2,6-dichloropyridine in the presence of a selected transition metal catalyst and a strong base.

A need exists for selectively converting 2,6-dichloropyridine to 2-chloropyridine since the dichloro product is an undesired by-product formed during the production of 2-chloropyridine by the chlorination of pyridine. A number of techniques have been disclosed for the hydrogenolysis of halobenzenes (see U.S. Pat. Nos. 2,725,405, 2,866,828 and 3,595,931) and U.S. Pat. No. 2,502,125 discloses a method for the preparation of monobromopyridine by the reduction of dibromopyridine. However, none of these teachings disclose or suggest the selective hydrogenolysis of 2,6-dichloropyridine to form 2-chloropyridine and more significantly none suggest the process of this invention.

Now it has been found that 2-chloropyridine can be economically and conveniently prepared by the liquid phase hydrogenolysis of 2,6-dichloropyridine in the presence of molecular hydrogen, a selected transition metal catalyst and a strong base.

The catalyst employed in the process of this invention is a transition metal and more particularly a transition metal selected from the group consisting of palladium, platinum and nickel with palladium being preferred. The catalyst metals can be self-supported or deposited on a support or carrier. Useful support or carrier materials include carbon, alumina, silica, barium sulfate, calcium carbonate, asbestos, bentonite, diatomaceous earth, fuller's earth and other analogous materials.

The base material used in the process of this invention may be any strong base and more particularly is a base selected from the group consisting of alkali metal hydroxides, alkaline earth metal hydroxides and alkyl amines of the formula $R_xNH_{3-x}$ where R is an alkyl of 1 to 4 carbon atoms and $x$ is 1 to 3. The alkali metal and alkaline earth metal hydroxides are the preferred base material with the hydroxides of sodium, potassium, lithium, cesium, rubidium, calcium and magnesium being particularly preferred from this group. Sodium hydroxide is most particularly preferred as the base material.

Generally, the reaction is carried out in the presence of a catalytic amount of the selected transition metal catalyst. More particularly, from about 0.0025 to about 10 percent by weight and preferably from about 0.025 to about 1 percent by weight of catalyst based on the weight of 2,6-dichloropyridine is used.

The base used in the reaction will generally be in liquid form and will be an aqueous solution when using an alkali or alkaline earth metal hydroxide. Said aqueous solution may have a concentration of up to about 75 percent by weight of the basic compound and preferably from about 10 to about 53 percent by weight. The amount of base can vary widely with at least 0.1 part by weight of said base per part by weight of 2,6-dichloropyridine being used and preferably from about 1 to about 10 parts of base per part of 2,6-dichloropyridine.

The amount of hydrogen employed in the reaction can be varied with a slight excess over stoichiometric quantities generally being used. More particularly, from about 0.1 to about 10 moles of hydrogen may be used per mole of 2,6-dichloropyridne with the preferred amount being at least 1 mole of hydrogen per mole of 2,6-dichloropyridine. The reaction temperature can suitably vary from about −10° to about 100°C and preferably from about 0° to about 30°C. Atmospheric pressure can suitably be employed, but pressures of from about 0.2 atmosphere to about 100 atmospheres and preferably from about 1 to about 10 atmospheres may be used.

While the use of a solvent is not necessary in carrying out the process of this invention, well-known organic solvents which will dissolve the 2,6-dichloropyridine may be used. Solvents of this type include aromatic hydrocarbons such as benzene, toluene and xylene; carbon tetrachloride; chloroform and pyridine with pyridine being a preferred solvent. Further illustrations of useful solvents may be found in "Organic Solvents" edited by Weissburger et al., Vol. VII, 2nd edition, 1955.

It is to be noted that the starting material used in this process is 2,6-dichloropyridine. One common way this material is obtained is as a predominant by-product in the chlorination of pyridine to form chloropyridine and while other forms of the dichloropyridine may also be present in minor proportions, the hydrogenolysis process of this invention is particularly applicable to such mixtures of by-products. The term 2,6-dichloropyridine as used in the specification and claims is intended to include mixtures of dichloropyridines having the 2,6-dichloropyridine as the predominent or major portion thereof.

While the reaction time for this process may be varied, it is desirable to stop the reaction after about 20 to about 80 percent conversion of the 2,6-dichloropyridine and preferably after from about 20 to about 50 percent conversion thereof.

It is generally desired to agitate the reaction mixture to keep the two layers thoroughly mixed (when using aqueous solution). Agitation may be provided by well-known mechanical means or by bubbling hydrogen through the system.

The following examples are further illustrative of the method of this invention.

EXAMPLE I

A reaction flask was charged with 20 grams of 2,6-dichloropyridine and 150 grams of pyridine and agitated and cooled to 3°C with an ice bath. After all the 2,6-dichloropyridine was dissolved, 50 grams of 25 percent caustic (NaOH) aqueous solution and 1 gram of 5 percent by weight palladium on carbon catalyst were added and the flask purged with nitrogen. Hydrogen gas was introduced and sparged into the liquids at 1 atmosphere pressure and at a rate of 500 cc. per minute. Samples of liquid were taken periodically and analyzed by vapor phase chromatography as follows:

| Reaction time hours | Conversion of 2,6,dichloropyridine | Yields 2-chloropyridine | Pyridine |
|---|---|---|---|
| 1 | 24% | 80% | 20% |
| 2 | 57% | 55% | 45% |
| 3 | 74% | 41% | 59% |
| 4 | 88% | 23% | 77% |

EXAMPLE II

The same procedure as in Example I was followed, substituting 50 percent caustic for the 25 percent caustic solution. Results are as follows:

| Reaction time hours | Conversion of 2,6-dichloropyridine | Yields 2-chloropyridine | Pyridine |
|---|---|---|---|
| 4 | 26% | 68% | 32% |
| 5 | 29% | 67% | 33% |

What is claimed is:

1. A process for preparing 2-chloropyridine comprising reacting hydrogen with 2,6-dichloropyridine at a temperature at −10° to 100°C by feeding hydrogen into a solution of said 2,6-dichloropyridine at least partially dissolved in a solvent selected from the group consisting of benzene, xylene, toluene, carbon tetrachloride and pyridine in the presence of at least 0.1 part by weight per part by weight 2,6-dichloropyridine of a base selected from the group consisting of an alkali or alkaline earth metal hydroxide and an alkyl amine of the formula $R_xNH_{3-x}$ wherein R is alkyl of 1 to 4 carbon atoms, and $x$ is 1–3, said base being provided as an aqueous solution having a concentration of up to about 75 percent by weight of said base and in the presence of a catalytic amount of a transition metal catalyst selected from the group consisting of palladium, platinum and nickel.

2. The process of claim 1 wherein a pressure in the range of 0.2 atmosphere to about 100 atmosphere is employed.

3. The process of claim 1 wherein said basic material is selected from the group consisting of alkali metal hydroxide and alkaline earth metal hydroxide.

4. The process of claim 3 wherein said alkali metal hydroxide is selected from the group consisting of sodium hydroxide, potassium hydroxide, lithium hydroxide, cesium hydroxide and rubidium hydroxide and said alkaline earth metal hydroxide is selected from the group consisting of calcium hydroxide and magensium hydroxide.

5. The process of claim 4 wherein from about 0.0025 to about 10 percent by weight of catalyst based on the weight of 2,6-dichloropyridine is used.

6. The process of claim 1 wherein palladium is said catalyst and sodium hydroxide is said base.

7. The process of claim 6 wherein pyridine is employed as a solvent.

8. The process of claim 7 wherein said reaction temperature is from about 0° to about 30°C., said pressure is from about 1 to about 10 atmospheres, said aqueous solution contains about 10 to about 53 percent by weight of sodium hydroxide, from about 1 to about 10 parts by weight of said sodium hydroxide per part by weight of 2,6-dichloropyridine is used and from about 0.025 to about 1 percent by weight of said catalyst based on the weight of 2,6-dichloropyridine is used.

* * * * *